(12) United States Patent
Chen et al.

(10) Patent No.: US 9,732,360 B2
(45) Date of Patent: Aug. 15, 2017

(54) METHOD FOR IMPROVING PRODUCTION OF BIO-HYDROGEN FROM WASTE WATER CONTAINING PROTEIN

(71) Applicant: TONGJI UNIVERSITY, Shanghai (CN)

(72) Inventors: Yinguang Chen, Shanghai (CN); Naidong Xiao, Shanghai (CN); Huaichen Wang, Shanghai (CN)

(73) Assignee: Tongji University, Shanghai (CN)

( * ) Notice: Subject to any disclaimer, the term of this patent is extended or adjusted under 35 U.S.C. 154(b) by 348 days.

(21) Appl. No.: 14/412,349

(22) PCT Filed: Jun. 21, 2013

(86) PCT No.: PCT/CN2013/077690
§ 371 (c)(1),
(2) Date: Dec. 31, 2014

(87) PCT Pub. No.: WO2014/005484
PCT Pub. Date: Jan. 9, 2014

(65) Prior Publication Data
US 2015/0184200 A1    Jul. 2, 2015

(30) Foreign Application Priority Data

Jul. 2, 2012    (CN) .......................... 2012 1 0223627

(51) Int. Cl.
| | | |
|---|---|---|
| *C02F 3/28* | (2006.01) |
| *C12P 5/00* | (2006.01) |
| *C12P 3/00* | (2006.01) |
| *C02F 1/32* | (2006.01) |
| *C02F 3/34* | (2006.01) |
| *C12N 1/20* | (2006.01) |
| *C02F 1/66* | (2006.01) |

(52) U.S. Cl.
CPC ........ *C12P 3/00* (2013.01); *C02F 1/32* (2013.01); *C02F 3/28* (2013.01); *C02F 3/348* (2013.01); *C12N 1/20* (2013.01); *C02F 1/66* (2013.01); *C02F 2209/30* (2013.01); *C02F 2301/10* (2013.01); *C02F 2303/10* (2013.01); *C02F 2305/06* (2013.01); *Y02W 10/30* (2015.05)

(58) Field of Classification Search
None
See application file for complete search history.

(56) References Cited

FOREIGN PATENT DOCUMENTS

| | | |
|---|---|---|
| CN | 101200338 A | 6/2008 |
| CN | 102286537 A | 12/2011 |
| CN | 102747106 A | 10/2012 |

OTHER PUBLICATIONS

International Search Report, mailed on Sep. 26, 2013, corresponding to PCT/CN2013/077690.
International Preliminary Report on Patentability, mailed on Jan. 6, 2015, corresponding to PCT/CN2013/077839.

*Primary Examiner* — Allison Fox
(74) *Attorney, Agent, or Firm* — Zareefa B. Flener; Flener IP Law

(57) ABSTRACT

Disclosed is a method for improving biological production of hydrogen from protein-containing wastewater comprising two stages: ultraviolet radiation pretreatment of protein-containing wastewater and biological production of hydrogen under a neutral pH condition and intermediate temperature condition.

5 Claims, 1 Drawing Sheet

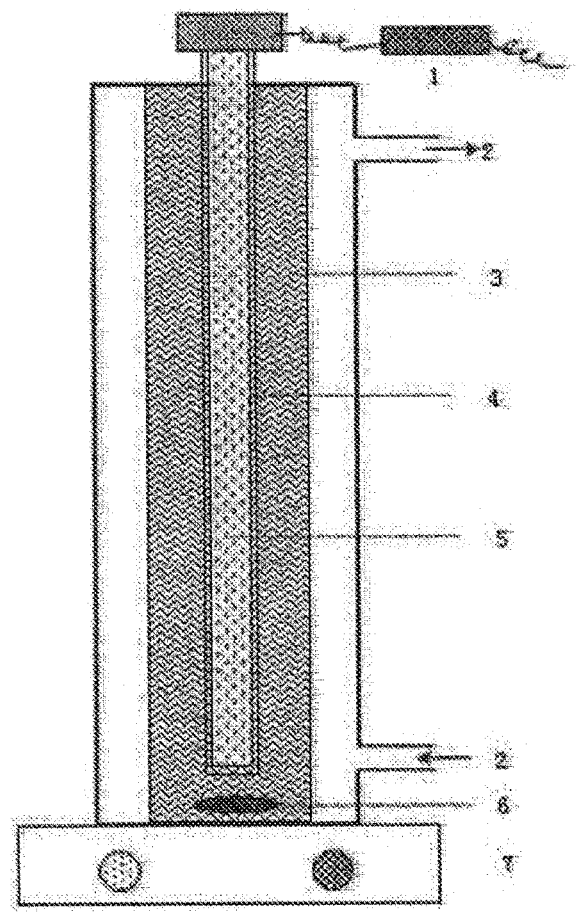

METHOD FOR IMPROVING PRODUCTION OF BIO-HYDROGEN FROM WASTE WATER CONTAINING PROTEIN

TECHNICAL FIELD

The present invention relates to the field of environmental protection technology and in particular relates to a method for improving biological production of hydrogen from protein.

BACKGROUND ART

At present, sewage treatment plants in urban areas produce a large a amount of excess sludge and in the meantime, food processing industry produce a large amount of industrial wastewater every year. In addition to carbohydrates and fats, protein is the major organic components of the excess sludge and wastewater from food processing industry. Proteins account for over 40% of the solid components of excess sludge (SS) and protein-containing wastewater is produced in large quantities in the process of food processing (e.g. soy, whey and fish). It is one of major issues in the field of environmental protection to make the excess sludge and sewage with high protein content be harmless and became useful resources. Meanwhile, hydrogen can be widely used as a kind of clean energy. There will be a broader prospect if the biological production of hydrogen via anaerobic fermentation of wastes with high protein content could be accompanied by making the wastes be harmless and become useful resources simultaneously.

Under anaerobic conditions, proteins can be firstly hydrolyzed into peptides and amino acids, and then converted into short-chain fatty acids with production of hydrogen gas in acidification stage. The products by acidification are finally converted into methane in methanation stage. To obtain hydrogen gas as an intermediate product, it is necessary to inhibit the activity of methanogenic bacteria and to restrict the fermentation process to the acidification stage and further to inhibit the activity of other hydrogen-consuming bacteria except methanogenic bacteria. However, unlike carbohydrates, protein has a slow rate of degradation and an incomplete degree of degradation under anaerobic conditions. The hydrolysis process is a rate limiting, step in the process of anaerobic degradation of proteins.

UV light, especially UV light-C, provides a kind of physical methods for protein denaturation. The natural structure of proteins can be damaged after absorption of UV light by tyrosine, tryptophan and phenylalanine in the proteins and protein unfolding may occur, which will facilitate protein hydrolysis and subsequent biological production of hydrogen.

SUMMARY OF THE INVENTION

The present invention aims to provide a method for improving biological production of hydrogen from protein-containing wastewater.

The method for improving biological production of hydrogen from protein-containing waste water raised by the present invention comprises the following steps:

Step (1): Ultraviolet Radiation Pretreatment of Protein-containing Wastewater

Add protein-containing wastewater into a UV light pretreatment apparatus, open UV light lamp with a ballast, perform UV light irradiation, maintain UV light irradiation intensity at 10-40 w/L wastewater and aqueous layer is 2-10 cm in thickness, meanwhile, open magnetic stirrer and circulating cooling water to maintain the protein-containing wastewater at a temperature of 20-25° C. in a process of the UV light irradiation, the UV light irradiation lasts for 0.5-10 hours to obtain pre-treated protein-containing wastewater;

Step (2): Biological Production of Hydrogen from the Pre-treated Protein-containing Wastewater Under Neutral pH Condition Add the pre-treated protein-containing wastewater obtained in step (1) to an anaerobic reactor, inoculate heat-treated anaerobic activated sludge, making concentration of activated sludge (SS) in the anaerobic reactor at 3500-4500 mg/L, and then add trace elements and chloroform to adjust pH value of mixture to neutral state, after nitrogen purging of the anaerobic reactor for 2 minutes, seal the anaerobic reactor with a rubber stopper to maintain it at anaerobic state, the anaerobic reactor undergoes anaerobic fermentation for 72-96 hours in shaker under intermediate temperature condition, measure volume and content of hydrogen gas in the anaerobic reactor once every 12 hours, and maintain pH value of solution in the anaerobic reactor at neutral state throughout the process;

Wherein, additive volume of the chloroform accounts for 0.01%-0.05% of volume of the protein-containing wastewater; and dosage of the trace elements accounts for 0.33% of the volume of the protein-containing wastewater.

In step (1) of the present invention, the UV light irradiation of the protein-containing wastewater lasts for 1-3 hours, the aqueous layer thickness is 2-4 cm.

In step (2) of the present invention, the additive volume of the chloroform accounts for 0.02%-0.03% of the volume of the protein-containing wastewater.

In the present invention, the heat-treated anaerobic activated sludge is sludge heated to boiling at a temperature of 102° C. for 30 minutes.

In step (2) of the present invention every 1 L of trace element solution contains 2.0 g, EDTA-2Na, 2.0 g $FeSO_4.7H_2O$, 0.1 g $H_3BO_3$, 0.1 g $CoCl_2.6H_2O$, 0.1 g $ZnCl_2$, 0.05 g $Cu(NO_3).5H_2O$, 0.1 g $MnCl_2.4H_2O$, 0.75 g $Na_2MoO_4$, 0.02 g $NiCl_2.6H_2O$ and 0.001 g $Na_2SeO_3$. Each of them is prepared with distilled water and total volume of them amounts to 1 L.

In step (2) of the present invention, pH value of the mixture is adjusted to neutral state by means of NaOH or HCL.

The present invention can achieve the following beneficial effects:

(1) It provides a method for improving biological production of hydrogen front protein, which combines UV light denaturation of proteins and biological production of hydrogen together with the result that protein conversion rate and hydrogen yield increases by 2.79 times, respectively:

(2) UV light radiation pretreatment of protein facilitates protein unfolding so as to change its conformation and make its structure become loose and further increase the number of cleavage sites of proteases during fermentation stage, thereby enhancing bio-availability of protein and generation of hydrogen gas. Compared with some other methods for protein denaturation, UV light radiation pretreatment doesn't produce any residue and doesn't cause secondary pollution, which has significant advantages.

(3) As compared to acidic or fermentation conditions, improvement of protein conversion rate and hydrogen gas yield under neutral, pH can dramatically reduce costs of agents in the process of treatment of protein-containing wastewater, and reduce the acidic and alkalic corrosion of fermentation equipments.

BRIEF DESCRIPTION OF THE DRAWINGS

The drawing shows the UV light pretreatment apparatus of the present invention for treatment of protein-containing wastewater.
In the drawing, 1—UV light lamp ballast, 2—circulating cooling water, 3—protein solution, 4—quartz tube, 5—UV light lamp, 6—magnetic stirrer's rotor, 7—magnetic stirrer.

DETAILED DESCRIPTIONS OF THE PREFERRED EMBODIMENTS

Detailed illustrations are further made in connection with the following specific embodiments. However, it should be understood that the embodiments listed below only intend to illustrate the present invention and shouldn't be regarded as comprising the whole content of the present invention.

In the following embodiments, the UV light pretreatment apparatus for treatment of protein-containing wastewater is shown in the drawing. When protein-containing wastewater is subject to UV light irradiation, the water-immersed UV light irradiation is adopted, in the mean time, the magnetic stirrer and the external circulating cooling water are opened simultaneously. The pre-treated protein-containing wastewater is obtained after a certain period of UV light irradiation.

Embodiment 1

300 mL, protein-containing wastewater of 5,000 mg/L COD, 5 g/L $NaHCO_3$ and 0.183 g/L $K_2HPO_3$ without UV light pretreatment is directly added to an anaerobic reactor as a blank control, the anaerobic activated sludge is inoculated after heat treatment (102° C., 30 minutes), making the concentration (SS) of the sludge in the reactor at 4000±200 mg/L, and then 1 ml trace elements and 0.02% (60 μL) volume ratio of chloroform are added, pH value of mixture is adjusted to 7±0.2 with NaOH or HCL. After nitrogen purging of the reactor for 2 minutes, the reactor is sealed with a rubber stopper to maintain it in an anaerobic state, then the reactor is put in a shaker with temperature of 36±1.0° C. and rotating speed at 140±2 rpm for anaerobic fermentation for a certain period of time. The volume and content of hydrogen gas in the reactor are both measured once every 12 hours, and pH value of solution in the reactor are maintained at neutral state using NaOH or HCL throughout the process.

After fermentation, the mixture is centrifuged at 4500 rpm for 15 minutes to get supernatant. The total amount of volatile acid in the supernatant is measured, which is 950.2 mg COD/L; the accumulative yield of hydrogen at 84 hours after fermentation is 19.6 mL/g COD.

Embodiment 2

Protein-containing wastewater which is the same as that in Embodiment 1 is added into a UV light pretreatment apparatus as is shown in the drawing. The protein-containing wastewater is subject to water-immersed UV light irradiation. The UV light irradiation intensity is maintained at 14 w/L wastewater with the thickness of aqueous layer reaching 3 cm. Meanwhile, magnetic stirrer and circulating cooling water are opened to maintain the protein-containing wastewater at a temperature of 20-25.degree. C. in the process of UV light irradiation. The pre-treated protein-containing wastewater is obtained after UV light irradiation for 0.5-5 hours and its properties are shown in Table 1.

300 mL protein-containing wastewater after pre-treatment for 2 hours is added into the anaerobic reactor for the production of hydrogen by fermentation. Other operations are the same as those in embodiment 1. After fermentation, the mixture is centrifuged at 4500 rpm for 15 minutes to get supernatant. The total amount of volatile acid in the supernatant is measured, which is 3600.4 mg COD/L; the accumulative yield of hydrogen at 84 hours after fermentation is 78.2 mL/g—COD.

TABLE 1

Comparison of properties of protein-containing wastewater before and after UV light irradiation

| Indicator [a] | Blank control | UV 0.5 h | UV 1 h | UV 2 h | UV 5 h |
|---|---|---|---|---|---|
| COD | 4960 ± 40 | 4960 ± 40 | 4940 ± 30 | 4920 ± 20 | 4910 ± 30 |
| VAFs | 9.8 | 19.7 | 22.5 | 24.9 | 25.2 |
| $NH_4^+$—N | N.D. | N.D. | N.D. | N.D. | N.D. |
| Absorbance at 280 nm | 0.207 | 0.357 | 0.475 | 0632 | 0.844 |

[a] The unit of COD, VAFs is mg-COD/L, the unit of $NH_4^+$—N is mg/L; the absorbance at 280 nm is the value of the solution after being diluted by 10-fold and is dimensionless.

Embodiment 3

The protein-containing wastewater is added to a UV light pre-treatment apparatus and the UV light irradiation intensity is maintained at 10 w/L wastewater, the thickness of aqueous layer is 2 cm, and UV light irradiation is carried out for 0.5 hours, and then 300 mL of pretreated solution is added to an anaerobic reactor to produce hydrogen by fermentation. Other operations are the same as those in Embodiment 2. After fermentation, the total amount of volatile acids in supernatant is measured, which is 1965.4 mg COD/L; the accumulative yield of hydrogen at 84 hours after fermentation is 45.5 mL/g—COD.

Embodiment 4

The protein-containing wastewater is added to a UV light pre-treatment apparatus and the UV light irradiation intensity is maintained at 40 w/L wastewater, the thickness of aqueous layer is 10 cm and UV light irradiation is carried out for 0.5 hours, and then 300 mL of pretreated solution is added to an anaerobic reactor to produce hydrogen by fermentation. Other operations are the same as those in Embodiment 2. After fermentation, the total amount of volatile acids in supernatant is measured, which is 1678.4 mg COD/L; the accumulative yield of hydrogen at 72 hours after fermentation is 39.2 mL/g—COD.

Embodiment 5

The protein-containing wastewater is added to a UV light pre-treatment apparatus and the UV light irradiation intensity is maintained at 10 w/L wastewater, the thickness of aqueous layer is 10 cm and UV light irradiation is carried out for 10 hours, and then 300 mL of pretreated solution is added to an anaerobic reactor to produce hydrogen by fermentation. Other operations are the same as those in Embodiment 2. After fermentation, the total amount of volatile acids in supernatant is measured, which is 2746.3 mg COD/L; the accumulative yield of hydrogen at 84 hours after fermentation is 57.2 mL/g—COD.

Embodiment 6

The protein-containing wastewater is added to a UV light pre-treatment apparatus and the UV light irradiation intensity is maintained at 14 w/L wastewater the thickness of aqueous layer 3 cm and UV light irradiation is carried out for 2 hours, and then 300 mL of pretreated solution is added to an anaerobic reactor to produce hydrogen by fermentation, and 0.01% (30 μL) chloroform is added to inhibit homoacetogenic bacteria, other operations are the same as those Embodiment 2. After fermentation, the total amount of volatile acids in supernatant is measured, which is 3557.9 mg COD/L; the accumulative yield of hydrogen at 84 hours after fermentation is 75.1 mL/g—COD.

Embodiment 7

The protein-containing wastewater is aided to a UV light pre-treatment apparatus and the UV light irradiation intensity is maintained at 14 w/L wastewater, the thickness of aqueous layer is 3 cm and UV light irradiation is carried out for 2 hours, and then 300 mL of pretreated solution is added to an anaerobic reactor to produce hydrogen by fermentation, and 0.05% (150 μL) chloroform is added to inhibit homoacetogenic bacteria, other operations are the same as those in Embodiment 2. After fermentation, the total amount of volatile acids in supernatant is measured, which is 3540.3 mg COD/L; the accumulative yield of hydrogen at 96 hours after fermentation is 77.0 mL/g—COD.

What is claimed is:

1. A method for improving biological production of hydrogen from protein containing wastewater comprising:
    a first step (1) of pre-treating wastewater by:
        providing a UV light pre-treatment apparatus, comprising:
            an exterior wall and an interior wall to form an outer chamber and an inner chamber;
            a UV light lamp that is placed inside the inner chamber;
            a ballast that is attached to one end of the UV lamp;
            a quartz tube that covers the main body of the UV light lamp;
            a magnetic stirrer with its rotor inside the inner chamber;
        adding the wastewater into the inner chamber to a height of 2-10 cm;
        turning on the UV light lamp with the ballast and exposing the wastewater to UV light irradiation from the UV light lamp;
        maintaining the UV light irradiation intensity at 10-40 w/L wastewater;
        activating the magnetic stirrer to stir the wastewater and circulating cooling water into the outer chamber to maintain the wastewater at a temperature of 20-25° C. during the UV light irradiation;
        continuing to expose the wastewater to the UV light irradiation for 0.5-10 hours to pretreat the wastewater;
    and a second step (2) of producing hydrogen by:
        providing an anaerobic reactor that is different from the UV light pre-treatment apparatus;
        adding the pre-treated wastewater obtained in step (1) to the anaerobic reactor;
        adding a heat-treated anaerobic active sludge, wherein the concentration of the heat-treated anaerobic active sludge (SS) in the anaerobic reactor reaches 3500-4500 mg/L;
        adding trace element solution and chloroform into the anaerobic reactor to obtain a mixture;
        adjusting pH value of the mixture to a pH of 7±0.2;
        providing nitrogen gas for purging of the anaerobic reactor for 2 minutes, and after that
        sealing the anaerobic reactor with a rubber stopper to maintain it at an anaerobic state;
        placing the anaerobic reactor on a shaker for anaerobic fermentation for 72-96 hours at a temperature of 36±1° C.;
        measuring volume and content of hydrogen gas in the anaerobic reactor every 12 hours, and
        maintaining the pH value of solution in the anaerobic reactor at pH 7±0.2 during the whole reaction;
        wherein additive volume of the chloroform accounts for 0.01%-0.05% of volume of the protein-containing wastewater; and dosage of the trace elements accounts for 0.33% of the volume of the protein-containing waste water; and
        wherein every one liter of the trace element solution contains 2.0 g EDTA-2Na, 2.0g $FeSO_4 \cdot 7H_2O$, 0.1 g $H_3BO_3$, 0.1 g $CoCl_2 \cdot 6H_2O$, 0.1 g $ZnCl_2$, 0.05 g $Cu(NO_3) \cdot 5H_2O$, 0.1 g $MnCl_2 \cdot 4H_2O$, 0.75 g $Na_2MoO_4$, 0.02g $NiCl_2 \cdot 6H_2O$ and 0.001 g $Na_2SeO_3$, each is prepared with distilled water and total volume is one liter.

2. The method for improving biological production of hydrogen from protein-containing wastewater according to claim 1, wherein the UV light irradiation of the protein-containing wastewater lasts for 1-3 hours, and the height of the protein-containing wastewater is 2-4 cm in step (1).

3. The method for improving biological production of hydrogen from protein-containing wastewater according to claim 1, wherein the additive volume of the chloroform accounts for 0.02%-0.03% of the volume of the protein-containing wastewater in step (2).

4. The method for improving biological production of hydrogen from protein-containing wastewater according to claim 1, wherein the heat-treated anaerobic active sludge is a sludge that is heated to a boiling state at a temperature of 102° C. for 30 minutes.

5. The method for improving biological production of hydrogen from protein-containing wastewater according to claim 1, wherein pH value of the mixture is adjusted by NaOH or HCl in step (2).

* * * * *